United States Patent [19]

Bernstein

[11] Patent Number: 5,916,885
[45] Date of Patent: Jun. 29, 1999

[54] TOPICAL ADMINISTRATION OF CERTAIN AZASPIRANES TO PREVENT OR TREAT SKIN CONDITIONS ASSOCIATED WITH HYPERPROLIFERATION OF SKIN CELLS AND/OR IMMUNOLOGICALLY MEDIATED DISORDERS

[76] Inventor: Lawrence R. Bernstein, 380 Willow Rd., Menlo Park, Calif. 94025

[21] Appl. No.: 08/902,503

[22] Filed: Jul. 29, 1997

Related U.S. Application Data

[62] Division of application No. 08/672,728, Jun. 28, 1996, Pat. No. 5,843,936.

[51] Int. Cl.$^6$ .................................................. A61K 31/555
[52] U.S. Cl. ............................ 514/184; 514/188; 514/189
[58] Field of Search ..................................... 514/184, 186, 514/188, 189

[56] References Cited

U.S. PATENT DOCUMENTS

| | | |
|---|---|---|
| 3,825,546 | 7/1974 | Rice . |
| 4,291,030 | 9/1981 | Mulinos . |
| 4,468,393 | 8/1984 | Geschickter . |
| 4,654,333 | 3/1987 | Tenoso . |
| 5,064,835 | 11/1991 | Bochis et al. . |
| 5,246,706 | 9/1993 | Chiang et al. ........................... 424/449 |

FOREIGN PATENT DOCUMENTS

| | | |
|---|---|---|
| 788 490 | 1/1973 | Belgium . |
| 0 201 804 | 11/1986 | European Pat. Off. . |
| 0 201 804 B1 | 11/1986 | European Pat. Off. . |
| 0 310 321 | 4/1989 | European Pat. Off. . |
| WO 92 02229 | 2/1992 | WIPO . |
| WO 94 04150 | 3/1994 | WIPO . |

OTHER PUBLICATIONS

Jack L. Arbiser (1996), "Angiogenesis and the Skin: a Primer," *J. Am Acad Dermatol U.S.*, 34(3):486–497.
Alison M. Badger et al. (1990), "Antiarthritic and Suppressor Cell Inducing Activity of Azaspiranes: Structure–Function Relationships of a Novel Class of Immunomodulatory Agents," *J. Med. Chem* 33:2963–2970.
Elizabeth Eisenhauer et al. (1985), "A Phase II Study of Spirogermanium in Patients with Metastatic Malignant Melanoma," *Investigational New Drugs* 3:303–305.
Bridget T. Hill et al (1982), "Cytotoxic Effects and Biological Activity of 2–Aza–8–germanspiro[4,5]–decane–2–propanamine–8,8–diethyl–N,N–dimethyl Dichloride (NSC 192965; Spirogermanium) in Vitro," *Cancer Research* 42(7):2852–2856.

Daniel N. Sauder et al. (1980), "Suppressor Cell Function in Psoriasis," *Arch. Dermatol.* 116:51–55.
Badger et al., "Generation of Suppressor Cells in Normal Rats by Treatment with Spirogermanium, a Novel Heterocyclic Anticancer Drug," *Immunopharmacology* 10:201–207 (1985).
Badger et al., "Antiarthritic and Suppressor Cell Inducing Activity of Azaspiranes: Structure–Function Relationships of a Novel Class of Immunomodulatory Agents," *J. Med. Chem.* 33:2963–2970 (1990).
Berardesca et al., "Non–invasive Evaluation of Topical Calcipotriol versus Clobetasol in the Treatment of Psoriasis," *Acta Derm Venereol* (Stokh) 74:302–304 (1994).
DiMartino et al., "Antiarthritic and Immunoregulatory Activity of Spirogermanium," *J. Pharmacol. and Exper. Therapeutics* 236(1):103–110.
Elias et al., "A Controlled Trial of Topical Propylthiouracil in the Treatment of Patients with Psoriasis," *J. Amer. Acad. Dermatol.* 31(3):455–458.
Highton et al., "Calcipotriene Ointment 0.005% for Psoriasis: A Safety and Efficacy Study," *J. Amer. Acad. Dermatol.* 32:(1):67–72 (1995).
Mirabelli et al., "Pharmacological Activities of Spirogermanium and Other Structurally Related Azaspiranes: Effects on Tumor Cell and Macrophage Functions," *Anti–Cancer Drug Design* 3:231–242 (1989).
Rice et al., "Spirans XXII. Synthesis of 4,4–Dialkyl–4–germacyclo–hexanone and 8,8–Dialkyl–8–germaazaspiro–[4,5]decanes," *J. Heterocyclic Chem.* 11:1041–1047 (1974).
Schein, P.S. et al., "Phase I Clinical Trial of Spirogermanium," *Cancer Treatment Reports*, vol. 64, No. 10–11, pp. 1051–1056 (Oct./Nov. 1980).
Slavik et al., "Spirogermanium: A New Investigational Drug of Novel Structure and Lack of Bone Marrow Toxicity," *Investigational New Drugs* 1:225–234 (1983).

*Primary Examiner*—Zohreh Fay
*Attorney, Agent, or Firm*—Dianne E. Reed; David W. Maher

[57] ABSTRACT

A locally administrable topical pharmaceutical composition is provided for prevention or treatment of skin conditions associated with hyperproliferation of skin cells and/or an immunologically mediated disorder, e.g., psoriasis, atopical dermatitis, contact dermatitis, seborrhoeic dermatitis, lupus and the like. The composition contains a topical carrier and spirogermanium or a structurally related azaspirane. Also provided are methods for using the novel composition and laminated patches which may be applied to the skin to administer the composition thereto.

9 Claims, No Drawings

TOPICAL ADMINISTRATION OF CERTAIN AZASPIRANES TO PREVENT OR TREAT SKIN CONDITIONS ASSOCIATED WITH HYPERPROLIFERATION OF SKIN CELLS AND/OR IMMUNOLOGICALLY MEDIATED DISORDERS

This application is a divisional of U.S. patent application Ser. No. 08/672,728, filed Jun. 28, 1996, now U.S. Pat. No. 5,843,936.

TECHNICAL FIELD

The present invention relates generally to the prevention or treatment of certain types of skin disorders. More particularly, the invention relates to the prevention or treatment of skin conditions associated with hyperproliferation of skin cells and/or immunologically mediated disorders, and involves topical administration of an azaspirane compound such as spirogermanium.

BACKGROUND

Spirogermanium was described by L. M. Rice et al.; see, e.g., U.S. Pat. No. 3,825,546 to Rice, which discloses the compound as a novel antihypertensive agent, and Rice et al., "Spirans XXII. Synthesis of 4,4-Dialkyl-4-germacyclohexanone and 8,8-Dialkyl-8-germaazaspiro-[4.5]decanes," *J. Heterocyclic Chem.* 11:1041–1047 (1974), in which the biological properties of the compound are examined in further detail. Syntheses of spirogermanium and related compounds, including silicon-substituted azaspiranes, were also disclosed by Rice, and involve the use of what were apparently novel azaspirodione intermediates.

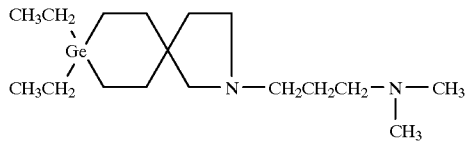

Spirogermanium

The dimethyl, diethyl, dipropyl and dibutyl derivatives of spirogermanium were later shown to be useful in a variety of contexts, including treatment of hypercholesterolemia (U.S. Pat. No. 4,291,030 to Mulinos), arthritis (U.S. Pat. No. 4,468,393 to Geschickter; Badger et al., "Antiarthritic and Suppressor Cell Inducing Activity of Azaspiranes: Structure-Function Relationships of a Novel Class of Immunomodulatory Agents," *J. Med. Chem.* 33:2963–2970 (1990); DiMartino et al., "Antiarthritic and Immunoregulatory Activity of Spirogermanium," *J. Pharmacol. and Exper. Theraipeutics* 236(1):103–110)), and multiple sclerosis (U.S. Pat. No. 4,654,333 to Tenoso). Anticancer activity for spirogermanium itself has also been suggested; see, e.g., Mirabelli et al., "Pharmacological Activities of Spirogermanium and Other Structurally Related Azaspiranes: Effects on Tumor Cell and Macrophage Functions," *Anti-Cancer Drug Design* 3:231–242 (1989), Slavik et al., "Spirogermanium: A New Investigational Drug of Novel Structure and Lack of Bone Marrow Toxicity," *Investigational New Drugs* 1:225–234 (1983), and Badger et al., "Generation of Suppressor Cells in Normal Rats by Treatment with Spirogermanium, a Novel Heterocyclic Anticancer Drug," *Immunopharmacology* 10:201–207 (1985).

Spirogermanium is currently available from Unimed, Inc., as the hydrochloride salt, under the trademark SPIRO-32®.

Spirogermanium HCl is a white powder which is freely soluble in water and in 95% ethanol, has a molecular weight of 414 and a melting point ranging from 284° C. to 288° C. Spirogermanium has been administered both by intravenous infusion and orally.

To date, topical administration of spirogermanium or related azaspirane compounds is unknown. The present invention is premised on the unexpected finding that topical administration of spirogermanium and related azaspiranes is extremely effective in addressing certain skin conditions associated with hyperproliferation of skin cells and/or an immunologically mediated disorder. specifically, it has now been discovered that spirogermanium and certain structurally related azaspiranes may be administered in topical formulations to prevent or treat a host of skin conditions, including psoriasis and various forms of dermatitis, including atopical dermatitis, contact dermatitis and seborrhoeic dermatitis.

SUMMARY OF THE INVENTION

Accordingly, it is a primary object of the invention to address the above-mentioned need in the art by providing pharmaceutical compositions, methods, and drug delivery systems for treating skin conditions associated with hyperproliferation of skin cells and/or an immunologically mediated disorder.

It is another object of the invention to provide novel topical pharmaceutical compositions containing spirogermanium or a structurally related azaspirane, in combination with a topical carrier.

It is still another object of the invention to provide a method for preventing or treating a skin condition associated with hyperproliferation of skin cells and/or an immunologically mediated disorder in an individual prone to or afflicted with such a condition, by topically administering a composition containing spirogermanium or a structurally related azaspirane to the affected area of the individual's skin.

It is a further object of the invention to provide novel drug delivery systems for carrying out the aforementioned method, particularly drug delivery systems in the form of laminated patches for application to the skin.

Additional objects, advantages and novel features of the invention will be set forth in part in the description which follows, and in part will become apparent to those skilled in the art upon examination of the following, or may be learned by practice of the invention.

DETAILED DESCRIPTION OF THE INVENTION

Before the present compositions, methods and drug delivery systems invention are disclosed and described, it is to be understood that this invention is not limited to specific formulations, i.e., specific carrier materials or the like, to specific dosage regimens or to specific drug delivery systems, as such may vary. It is also to be understood that the terminology used herein is for the purpose of describing particular embodiments only and is not intended to be limiting.

It must be noted that, as used in the specification and the appended claims, the singular forms "a", "an" and "the" include plural referents unless the context clearly dictates otherwise. Thus, for example, reference to "an azaspirane" includes mixtures of such compounds, reference to "a carrier" includes mixtures of two or more carriers, and the like.

The term "topical administration" is used in its conventional sense to mean delivery of a topical drug or pharmacologically active agent to the skin or mucosa, as in, for example, the treatment of various skin disorders.

By the term "drug" or the term "pharmacologically active agent" as used herein is meant a chemical material or compound suitable for topical administration and which induces the desired effect.

By the term "effective" amount of a drug is meant a nontoxic but sufficient amount of a compound, to provide the desired local effect and performance at a reasonable benefit/risk ratio attending any medical treatment.

The term "topical vehicle" or "topical carrier" as used herein refers to a vehicle suitable for topical application of a drug, and includes any such materials known in the art, e.g., any liquid or nonliquid carrier, gel, cream, ointment, lotion, paste, emulsifier, solvent, liquid diluent, powder, or the like, which is stable with respect to all components of the topical pharmaceutical formulation.

The terms "azaspirane," "azaspirane compound" and "azaspirane derivative" are used interchangeably herein to refer to compounds encompassed by structural formula (I)

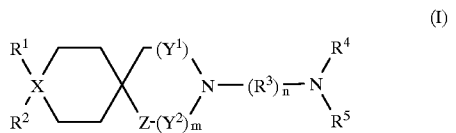

(I)

wherein:

$R^1$ and $R^2$ may be the same or different and are each selected from the group consisting of hydrogen and lower alkyl;

X is selected from the group consisting of Ge, Si, C and Sn;

$Y^1$ and $Y^2$ are the same and are either $CH_2$ or $C=O$;

m is zero or one;

Z is $CH_2$ when m is 1 and $CH_2$ or $C=O$ when m is zero;

$R^3$ is alkylene or alkenylene;

n is an integer in the range of 2 to 6 inclusive when $R^3$ is alkylene and 3 to 6 inclusive when $R^3$ is alkenylene; and $R^4$ and $R^5$ are independently selected from the group consisting of lower alkyl or lower alkenyl, or are linked together to form a heterocyclic group selected from morpholino, pyrrolidino, piperidino and lower alkyl substituted piperazino in which the lower alkyl group is attached to a terminal nitrogen atom.

The term "lower alkyl" as used herein in the description of chemical structures is intended to encompass alkyl groups having 1 through 6, preferably 1 through 4, carbon atoms.

In one embodiment of the invention, then, a locally administrable topical pharmaceutical composition is provided for the prevention or treatment of skin conditions associated with hyperproliferation of skin cells and/or an immunologically mediated disorder. These skin conditions are exemplified by, but not limited to: psoriasis; atopical dermatitis; contact dermatitis and further eczematous dermatitises; seborrhoeic dermatitis; Lichen planus; Pemphigus; bullous Pemphigoid, epidermolysis bullosa, urticaria, angioedemas, vasculitides; erythemas; cutaneous eospinphilias; Lupus erythematoses; and Alopecia areata. See, e.g., U.S. Pat. No. 5,064,835 to Bochis et al. The topical pharmaceutical formulation of the invention may also be useful in the treatment of actinic keratosis and skin cancer. Skin conditions of particular interest herein are psoriasis, atopical dermatitis, contact dermatitis, seborrhoeic dermatitis and lupus, most particularly psoriasis itself. While not wishing to be bound by theory, applicant believes that the present invention is effective against such conditions and disorders by virtue of inhibiting the underlying disease process rather than by treating the inflammation and other symptoms. In this regard, the invention appears to act both to inhibit underlying autoimmune responses and to directly inhibit hyperproliferation of skin cells.

The locally administrable topical pharmaceutical composition includes a topical carrier and either spirogermanium or a related azaspirane, i.e., a compound having the structure of formula (I)

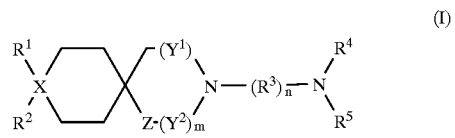

(I)

wherein:

$R^1$, $R^2$, $R^3$, $R^4$, $R^5$, $Y^1$, $Y^2$, Z, m and n are as defined above.

Examples of particular compounds of interest are wherein "X" is germanium, such as in spirogermanium itself, and wherein "X" is carbon or silicon.

The compounds may be administered as the free base or present in the form of an acid addition salt. Acid addition salts may be prepared from the free base using conventional means, which generally involve reaction of the free base with a suitable acid. Typically, the free base is dissolved in a polar organic solvent such as methanol or ethanol and the acid is added at a temperature of about 0° C. to about 100° C., preferably at ambient temperature. The resulting salt either precipitates or may be brought out of solution by addition of a less polar solvent. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like.

The topical carrier, as noted above, is one which is generally suited to topical drug administration and includes any such materials known in the art. The topical carrier is selected so as to provide the composition in the desired form, e.g., as a liquid, lotion, cream, paste, gel, powder, or ointment, and may be comprised of a material of either naturally occurring or synthetic origin. It is essential, clearly, that the selected carrier not adversely affect the active agent or other components of the topical formulation. Examples of suitable topical carriers for use herein include water, alcohols and other nontoxic organic solvents, glycerin, mineral oil, silicone, petroleum jelly, lanolin, fatty acids, vegetable oils, parabens, waxes, and the like. The composition of the invention may also be administered in the form of a shampoo, in which case conventional components of such a formulation are included as well, e.g., surfactants, conditioners, viscosity modifying agents, humectants, and the like.

Particularly preferred formulations herein are colorless, odorless ointments, lotions, creams and gels.

Ointments are semisolid preparations which are typically based on petrolatum or other petroleum derivatives. The specific ointment base to be used, as will be appreciated by those skilled in the art, is one that will provide for optimum drug delivery, and, preferably, will provide for other desired characteristics as well, e.g., emolliency or the like. As with other carriers or vehicles, an ointment base should be inert, stable, nonirritating and nonsensitizing. As explained in *Remington: The Science and Practice of Pharmacy*, 19th Ed. (Easton, Pa.: Mack Publishing Co., 1995), at pages 1399–1404, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (OW) emulsions, and include, for example, cetyl alcohol, glyceryl monostearate, lanolin and stearic acid. Preferred water-soluble ointment bases are prepared from polyethylene glycols of varying molecular weight; again, reference may be had to *Remington: The Science and Practice of Pharmacy* for further information.

Lotions are preparations to be applied to the skin surface without friction, and are typically liquid or semiliquid preparations in which solid particles, including the active agent, are present in a water or alcohol base. Lotions are usually suspensions of solids, and preferably, for the present purpose, comprise a liquid oily emulsion of the oil-in-water type. Lotions are preferred formulations herein for treating large body areas, because of the ease of applying a more fluid composition. It is generally necessary that the insoluble matter in a lotion be finely divided. Lotions will typically contain suspending agents to produce better dispersions as well as compounds useful for localizing and holding the active agent in contact with the skin, e.g., methylcellulose, sodium carboxymethyl-cellulose, or the like. A particularly preferred lotion formulation for use in conjunction with the present invention contains propylene glycol mixed with a hydrophilic petrolatum such as that which may be obtained under the trademark Aquaphor® from Beiersdorf, Inc. (Norwalk, Conn.).

Creams containing the selected azaspirane derivative are, as known in the art, viscous liquid or semisolid emulsions, either oil-in-water or water-in-oil. Cream bases are water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation, as explained in Remington, supra, is generally a nonionic, anionic, cationic or amphoteric surfactant.

Gels formulations are preferred for application to the scalp. As will be appreciated by those working in the field of topical drug formulation, gels are semisolid, suspension-type systems. Single-phase gels contain organic macromolecules distributed substantially uniformly throughout the carrier liquid, which is typically aqueous, but also, preferably, contain an alcohol and, optionally, an oil.

Shampoos for treating psoriasis and other skin conditions associated with hyperproliferation and/or an immunologically mediated disorder may be formulated with the selected azaspirane derivative and standard shampoo components, i.e., cleansing agents, thickening agents, preservatives, and the like, with the cleansing agent representing the primary ingredient, typically an anionic surfactant or a mixture of an anionic and an amphoteric surfactant.

Various additives, known to those skilled in the art, may be included in the topical formulations of the invention. For example, solvents may be used to solubilize certain drug substances. Other optional additives include skin permeation enhancers, opacifiers, anti-oxidants, gelling agents, thickening agents, stabilizers, and the like. Other agents may also be added, such as antimicrobial agents, antifungal agents, antibiotics and anti-inflammatory agents such as steroids.

In the preferred topical formulations of the invention, the active azaspirane agent is present in an amount which is generally less than 10% by weight of the total composition, preferably less than about 1% by weight, and most preferably less than about 0.1% by weight.

The topical compositions of the invention may also be delivered to the skin using conventional "transdermal"-type patches, wherein the drug composition is contained within a laminated structure that serves as a drug delivery device to be affixed to the skin. In such a structure, the drug composition is contained in a layer, or "reservoir," underlying an upper backing layer. The laminated structure may contain a single reservoir, or it may contain multiple reservoirs. In one embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. The particular polymeric adhesive selected will depend on the particular drug, vehicle, etc., i.e., the adhesive must be compatible with all components of the drug-containing composition. In an alternative embodiment, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form.

The backing layer in these laminates, which serves as the upper surface of the device, functions as the primary structural element of the laminated structure and provides the device with much of its flexibility. The material selected for the backing material should be selected so that it is substantially impermeable to the drug and to any other components of the drug-containing composition, thus preventing loss of any components through the upper surface of the device. The backing layer may be either occlusive or nonocclusive, depending on whether it is desired that the skin become hydrated during drug delivery. The backing is preferably made of a sheet or film of a preferably flexible elastomeric material. Examples of polymers that are suitable for the backing layer include polyethylene, polypropylene, polyesters, and the like.

During storage and prior to use, the laminated structure includes a release liner. Immediately prior to use, this layer is removed from the device to expose the basal surface thereof, either the drug reservoir or a separate contact adhesive layer, so that the system may be affixed to the skin. The release liner should be made from a drug/vehicle impermeable material.

Such devices may be fabricated using conventional techniques, known in the art, for example by casting a fluid admixture of adhesive, drug and vehicle onto the backing layer, followed by lamination of the release liner. Similarly, the adhesive mixture may be cast onto the release liner, followed by lamination of the backing layer. Alternatively, the drug reservoir may be prepared in the absence of drug or excipient, and then loaded by "soaking" in a drug/vehicle mixture.

As with the topical formulations of the invention, the drug composition contained within the drug reservoirs of these laminated system may contain a number of components. In some cases, the drug may be delivered "neat," i.e., in the absence of additional liquid. In most cases, however, the drug will be dissolved, dispersed or suspended in a suitable pharmaceutically acceptable vehicle, typically a solvent or gel. Other components which may be present include preservatives, stabilizers, surfactants, and the like.

Both the topical formulations and the laminated drug delivery systems may in addition contain a skin permeation enhancer. That is, because the inherent permeability of the skin to some drugs may be too low to allow therapeutic levels of the drug to pass through a reasonably sized area of unbroken skin, it is necessary to coadminister a skin permeation enhancer with such drugs. Suitable enhancers are well know in the art and include, for example, dimethylsulfoxide (DMSO), dimethyl formamide (DMF), N,N-dimethylacetamide (DMA), decylmethylsulfoxide ($C_{10}MSO$), $C_2$–$C_6$ alkanediols, and the 1-substituted azacycloheptan-2-ones, particularly 1-n-dodecylcyclazacycloheptan-2-one (available under the trademark Azone® from Whitby Research Incorporated, Richmond, Va.), alcohols, and the like.

The topical compositions and drug delivery systems of the invention can be used in the prevention or treatment of the skin conditions identified above. When used in a preventive method, susceptible skin is treated prior to any visible lesions on areas known to be susceptible to such lesions in a particular individual. In treating skin conditions associated with hyperproliferation of skin cells and/or an immunologically mediated disorder, it will be recognized by those skilled in the art that the optimal quantity and spacing of individual dosages of compounds of Formula (I) will be determined by the nature and extent of the condition being treated, the form, route and site of administration, and the particular individual undergoing treatment, and that such optimums can be determined by conventional techniques. It will also be appreciated by one skilled in the art that the optimal dosing regimen, i.e., the number of doses of spirogermanium or an analog thereof encompassed by the generic structure of Formula (I), can be ascertained using conventional course of treatment determination tests. Generally, a dosing regimen will involve administration of the selected topical formulation at least once daily, and preferably one to four times daily, until the psoriatic or other symptoms have subsided.

The practice of the present invention will employ, unless otherwise indicated, conventional techniques of drug formulation, particularly topical drug formulation, which are within the skill of the art. Such techniques are fully explained in the literature. See *Remington: The Science and Practice of Pharmacy*, cited supra, as well as Goodman & Gilman's *The Pharmacological Basis of Therapeutics*, 9th Ed. (New York: McGraw-Hill, 1996).

All patents, patent documents, and publications cited herein are hereby incorporated by reference in their entirety for their disclosure concerning any pertinent information not explicitly included herein.

It is to be understood that while the invention has been described in conjunction with the preferred specific embodiments thereof, the foregoing description, as well as the examples which follow, are intended to illustrate and not limit the scope of the invention. Other aspects, advantages and modifications will be apparent to those skilled in the art to which the invention pertains.

The following examples are put forth so as to provide those of ordinary skill in the art with a complete disclosure and description of how to make and use the compounds of the invention, and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in °C. and pressure is at or near atmospheric.

All solvents were purchased as HPLC grade and, where appropriate, solvents and reagents were analyzed for purity using common techniques. All reactions were routinely conducted under an inert atmosphere of argon, unless otherwise indicated.

EXAMPLE 1

Evaluation of Spirogermanium to Treat Psoriasis: Mitotic Activity of Epidermal Keratinocytes The mitotic activity of epidermal keratinocytes is one of the most obvious histological features of the psoriatic lesion. Many cytotoxic drugs used to treat the disease are believed to function by direct inhibition of keratinocyte replication. Spirogermanium ("SG") affects this aspect of epidermal metabolism, in view of its demonstrated effects on tumor cells.

Human foreskin keratinocytes were cultured in KGM. When the dishes were approximately 50% covered by cells, SG was added to give final concentrations of $5\times10^{-5}$ to $5\times10^{-9}$M. After 3 days, the cells were pulsed with $^3$H-TdR for 4 hours, and incorporation into DNA assayed by conventional means. The inhibition of incorporation in 2 experiments was as follows:

| Concentration of SG | Incorporation (as % of control) |
|---|---|
| $5 \times 10^{-5}$ M (2.0 µg/ml) | 0, 0 |
| $5 \times 10^{-6}$ M (0.2 µg/ml) | 0, 0 |
| $5 \times 10^{-7}$ M (0.02 µg/ml) | 30, 29 |
| $5 \times 10^{-8}$ M (0.002 µg/ml) | 44, 50 |
| $5 \times 10^{-9}$ M (0.0002 µg/ml) | 100 |

Thus, SG inhibited DNA synthesis at concentrations as low as $10^{-8}$M. This result indicates that spirogermanium is a very potent inhibitor of DNA synthesis in keratinocytes, and thus a very potent inhibitor of keratinocyte proliferation, suggesting that spirogermanium is a highly effective agent in treating psoriasis and other such skin disorders.

EXAMPLE 2

Evaluation of Spirogermanium: Effect on Endothelial Cells

Skin endothelial cells in psoriasis are intimately involved in initiating the inflammatory response. Agents which affect both the binding of T lymphocytes and the hyperproliferation of endothelial cells would be expected to have a major effect in controlling the skin lesions.

In this study, human skin microvascular endothelial cells were isolated both from foreskins removed at circumcision and from skin obtained following a facial cosmetic correction. The endothelial cells were grown in a modified Iscove's medium, and while in the growth phase, the effect of varying concentrations of spirogermanium was studied on both the morphology and the growth of the endothelial cell cultures. Final concentrations of spirogermanium in the growth medium were 1,000, 500, 100, 50, 10, 1.0 and 0.125 µg/ml.

| Concentration of SG (μg/ml) | Degree of Confluence |
|---|---|
| Control | 4+ (5 × 10⁴ cells/dish) |
| 1000 | 0 |
| 500 | 0 |
| 100 | 0 |
| 50 | 0 |
| 10 | 0 |
| 1.0 | 3+ (3 × 10⁴ cells/dish) |
| 0.125 | 4+ (5 × 10⁴ cells/dish) |

These studies showed a profound cytopathic effect of spirogermanium at all concentrations above 1.0 μg/ml. At the highest concentrations endothelial cells immediately rounded up and detached from the dish surface. At 10 μg/ml, vacuolization was observed before desquamation and ultimate cell death. At a concentration of 0.125 μg/ml, cell death was observed after 1 week. These results indicate that spirogermanium will be highly effective in the treatment of psoriasis and like skin disorders.

EXAMPLE 3

Compounds encompassed by structural formula (I) are evaluated in vivo for their efficacy in treating psoriasis. The methods of the following references are used in the evaluation: Berardesca et al., "Non-invasive Evaluation of Topical Calcipotriol versus Clobetasol in the Treatment of Psoriasis," *Acta Derm Venereol* (*Stokh*) 74:302–304 (1994); Elias et al., "A Controlled Trial of Topical Propylthiouracil in the Treatment of Patients with Psoriasis," *J. Amer. Acad. Dermatol.* 31(3):455–458; and Highton et al., "Calcipotriene Ointment 0.005% for Psoriasis: A Safety and Efficacy Study," *J. Amer. Acad. Dermatol.* 32(1):67–72 (1995). Experimental work conducted according to the documented procedures shows that spirogermanium and other compounds of formula (I) are effective for treating moderate to severe psoriasis.

I claim:

1. A drug delivery system for administering a pharmaceutical composition to the skin, in the form of a laminated composite comprising a backing layer that is substantially impermeable to the drug, and a drug reservoir containing a pharmaceutical composition comprising a compound having the structure of formula (I)

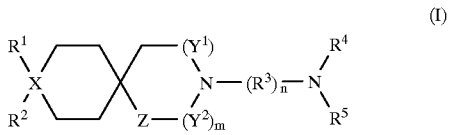

wherein:
$R^1$ and $R^2$ may be the same or different and are each selected from the group consisting of hydrogen and lower alkyl;
X is selected from the group consisting of Ge, Si, C and Sn;
$Y^1$ and $Y^2$ are the same and are either $CH_2$ or $C=O$;
m is zero or one;
Z is $CH_2$ when m is 1 and $CH_2$ or $C=O$ when m is zero;
$R^3$ is alkylene or alkenylene;
n is an integer in the range of 2 to 6 inclusive when $R^3$ is alkylene and 3 to 6 inclusive when $R^3$ is alkenylene; and
$R^4$ and $R^5$ are independently selected from the group consisting of lower alkyl or lower alkenyl, or are linked together to form a heterocyclic group selected from morpholino, pyrrolidino, piperidino and lower alkyl substituted piperazino in which the lower alkyl group is attached to a terminal nitrogen atom, or an acid addition salt thereof.

2. The drug delivery system of claim 1, wherein the drug reservoir comprises a polymeric matrix of a pharmaceutically acceptable contact adhesive material that serves to affix the system to the skin during drug delivery.

3. The drug delivery system of claim 1, further including a layer of a pharmaceutically acceptable skin contact adhesive material which defines the basal surface of the device and serves to affix the device to the skin during drug delivery.

4. The drug delivery system of claim 1, wherein, in the compound of formula (I), X is germanium.

5. The drug delivery system of claim 4, wherein the compound of formula (I) is spirogermanium.

6. The drug delivery system of claim 2, wherein, in the compound of formula (I), X is germanium.

7. The drug delivery system of claim 6, wherein the compound of formula (I) is spirogermanium.

8. The drug delivery system of claim 3, wherein, in the compound of formula (I), X is germanium.

9. The drug delivery system of claim 8, wherein the compound of formula (I) is spirogermanium.

* * * * *